United States Patent [19]

Madden et al.

[11] Patent Number: 5,690,536
[45] Date of Patent: Nov. 25, 1997

[54] BRASSIERE LINER

[76] Inventors: Kathleen A. D. Madden; Michael P. Madden, both of 10765 Cedarwood Drive, Waldorf, Md. 20601

[21] Appl. No.: 575,481

[22] Filed: Dec. 20, 1995

[51] Int. Cl.$^6$ ............................................. A41D 27/12
[52] U.S. Cl. ........................... 450/37; 450/52; 2/267
[58] Field of Search ........................... 450/1, 37, 53, 450/54, 55, 56, 57, 64, 65, 66, 67; 2/267, 268; 602/60, 61; 128/890

[56] References Cited

U.S. PATENT DOCUMENTS

| | | |
|---|---|---|
| D. 347,278 | 5/1994 | Higa . |
| 2,520,225 | 8/1950 | Scott-Elliot ........................... 450/67 |
| 4,047,534 | 9/1977 | Thomaschefsky et al. . |
| 4,074,721 | 2/1978 | Smits et al. . |
| 4,125,114 | 11/1978 | Repke . |
| 4,164,228 | 8/1979 | Weber-Unger . |
| 4,193,404 | 3/1980 | Repke . |
| 4,674,510 | 6/1987 | Sneider . |
| 4,700,699 | 10/1987 | Tollerud et al. . |
| 4,875,492 | 10/1989 | Mitchell et al. . |
| 5,017,174 | 5/1991 | Gowrylow . |
| 5,149,336 | 9/1992 | Clarke et al. . |
| 5,269,720 | 12/1993 | Moretz et al. . |

FOREIGN PATENT DOCUMENTS

| | | |
|---|---|---|
| 2064961 | 6/1981 | United Kingdom . |
| 2268687 | 1/1994 | United Kingdom . |

*Primary Examiner*—Jeanette E. Chapman
*Attorney, Agent, or Firm*—Chase & Yakimo

[57] ABSTRACT

Disposable bra liners comprising three cup-shaped coextensive layers attached together, with each layer presenting a circular periphery. The first layer is formed of wicking material for wicking away moisture into the second absorbent layer which is attached to the outer surface of the first layer. The third moisture resistant layer is attached to the outer surface of the absorbent layer. The bra liners further include a structural member attached to the layers for maintaining the shape of the pad. The structural member includes an elastic band attached to the layers at their peripheries and preferably has a plurality of spaced apart fold portions which taper inwardly from the band to present substantially V-shaped fold portions. Each layer preferably further includes a plurality of similar spaced apart fold portions formed therein.

18 Claims, 5 Drawing Sheets

BRASSIERE LINER

FIELD OF THE INVENTION

This invention relates to multi-layer disposable brassiere (bra) liners for nursing mothers. More specifically, the bra liners maintain their shape and positioning while being worn and prevent breast milk leakage from seeping into and through a mother's clothing.

BACKGROUND OF THE INVENTION

Devices for preventing breast milk leakage from contacting and seeping into and through clothing are currently available on the market. Generally, these devices fall into two broad categories, nursing or breast pads and nursing or protective brassieres. These two broad categories each comprise two general sub-categories, reusable pads and disposable pads, and unitary brassieres and brassieres having replaceable absorbent pads. Each of the devices currently comprising these categories suffers from at least one disadvantage, including low moisture absorbency, visibility of the device through clothing, bulkiness, inability to keep the moisture of the breast milk away from both the skin and clothing, poor fit within the brassiere, failure to maintain the proper shape within the brassiere, and lack of multiple sizes for accommodating women's differently sized breasts.

SUMMARY OF THE INVENTION

Accordingly, a primary object of the subject invention is to provide disposable, multi-layer, cup-shaped bra pads for nursing women which include a structural member that prevents the pad from shifting or moving out of its desired position after placement within a bra cup.

Another object of the subject invention is to provide bra liners that include a wicking layer, absorbent layer and moisture resistant layer, each having fold portions making the liners size adjustable.

Yet another object of the subject invention is to provide bra liners that include an innermost layer that wicks away breast milk leakage from the nursing mother's skin and an outermost moisture resistant layer that prevents the leakage from being absorbed by the nursing mother's clothing.

A further object of the subject invention is to provide bra liners including an absorbent layer capable of absorbing a large amount of leakage without being too bulky.

Still a further object of the subject invention is to provide bra liners that are easy to manufacture in various sizes.

These objects are attained by providing disposable bra liners or pads, comprising three cup-shaped coextensive layers attached together, with each layer presenting a circular periphery. The first layer is formed of wicking material for wicking away moisture into the second absorbent layer which is attached to the outer surface of the first layer. The third moisture resistant layer is attached to the outer surface of the absorbent layer for preventing leakage from being absorbed by the wearer's clothing. A structural member is attached to the layers for maintaining the shape of the liner. The structural member includes an elastic band attached to the layers at their peripheries and preferably has a plurality of spaced apart fold portions tapering inwardly from the band to present substantially V-shaped fold portions. Similar fold portions are also preferably formed in each of the layers.

Other objects and advantages of this invention will become apparent from the following description taken in connection with the accompanying drawings, wherein is set forth by way of illustration and example, an embodiment of this invention.

DETAILED DESCRIPTION

Figure 1:
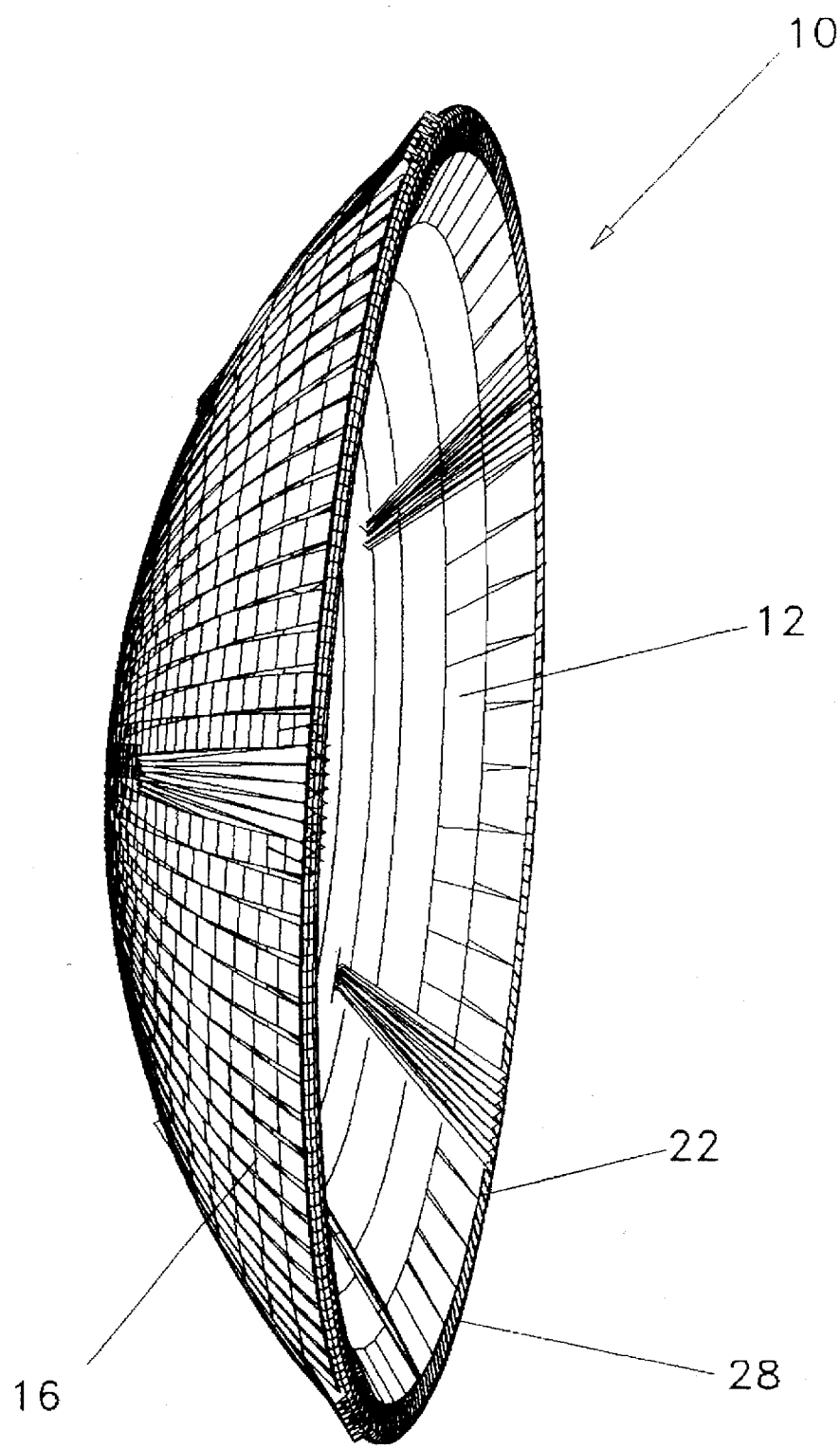
FIG. 1 is a side perspective view of a bra liner in accordance with the present invention.

Brassiere liner 10, as seen in FIG. 1, is for use by nursing mothers. Bra liner 10 is cup-shaped to conform comfortably to the shape of the mother's breasts and in use is simply inserted into the cup of a bra. Bra liner 10 preferably includes three layers 12, 14 and 16 and a structural member 18. See FIG. 2. First or proximal layer 12, relative to the wearer, wicks away breast milk leakage from the mother's skin into the second intermediate absorbent layer 14. The third or distal layer 16, relative to the wearer, is moisture resistant and prevents the leakage from being absorbed by the mother's clothing. Structural member 18 maintains the liner's shape to increase its comfort and enhance its performance.

Each layer 14, 16 and 18 is coextensive with the other layers and thus, is substantially the same size and cup shape. Of course the innermost layer 12 will be slightly smaller than the middle and outer layers 14 and 16, and the middle layer 14 is slightly smaller than outer layer 16 so that each layer 12, 14 and 16 fits immediately adjacent and engages the next layer in a nesting relationship, as in FIG. 1. Each layer 12, 14 and 16 presents an outer circular periphery 22, 24 and 26. See FIG. 2.

Layers 12, 14 and 16 are preferably bonded together in any conventional manner with the inner wicking layer 12 bonded to the outer moisture resistant layer 16 at their corresponding peripheries 22 and 26 to form an envelope in which the middle absorbing layer 14 and structural member 18 are contained. Alternatively, the middle absorbent layer 14 may be bonded to the inner wicking layer 12 to improve the wicking action of wicking layer 12 to the absorbent layer 14. To facilitate the bonding of inner wicking layer 12 to outer moisture resistant layer 16, wicking layer 12 includes a lip 28 that extends substantially perpendicularly outwardly from its outer periphery 22 into contact with outer periphery 26 of outer moisture resistant layer 16.

Figure 2:
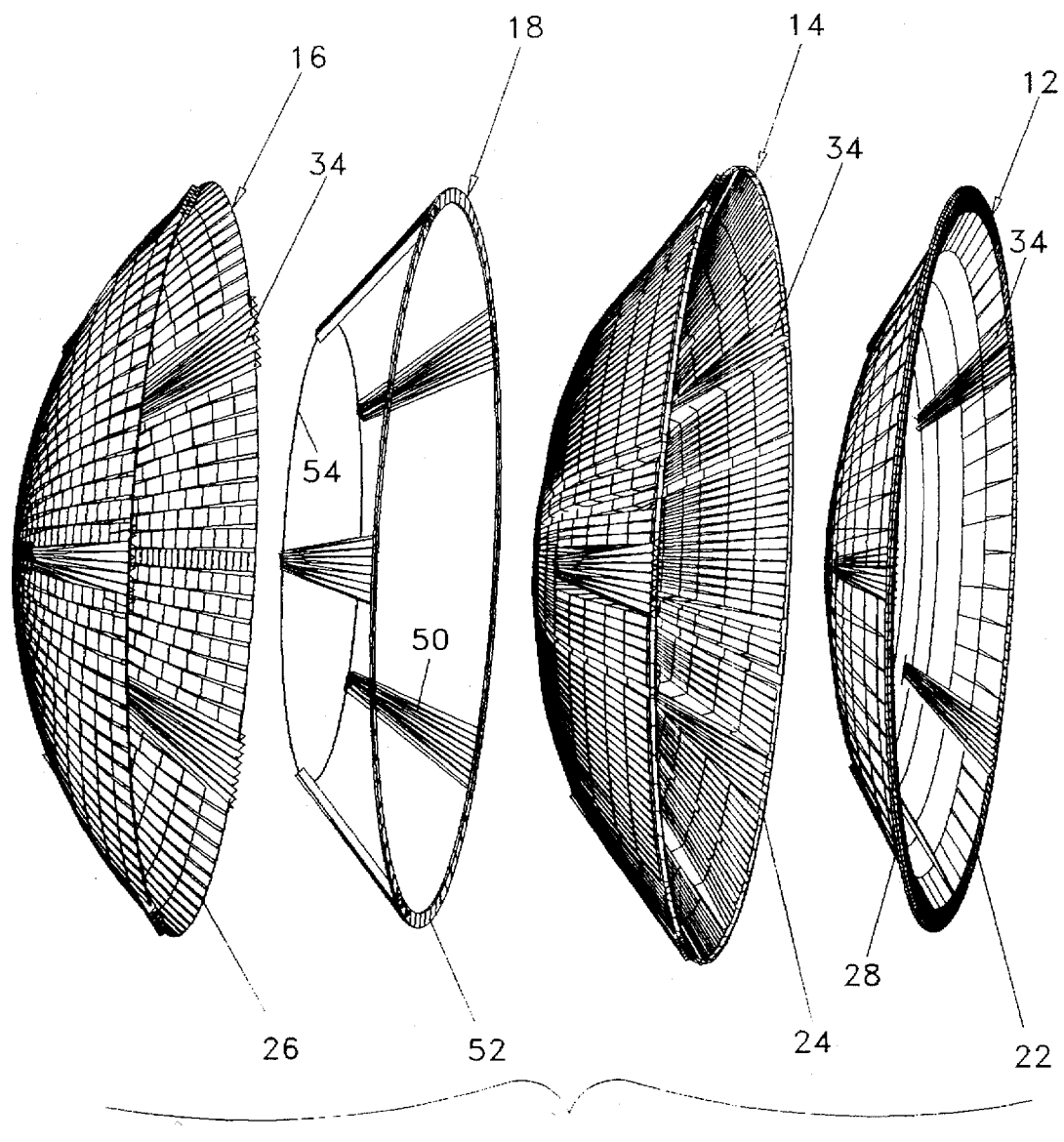
FIG. 2 is an exploded side perspective view of the bra liner of FIG. 1.

Each layer 12, 14 and 16 also preferably includes its own corresponding set of evenly spaced apart substantially V-shaped fold portions 34, as seen in FIG. 2. Fold portions 34 present accordion type folds which extend from the outer peripheries 22, 24 and 26 of layers 12, 14 and 16 inwardly toward the center of each layer 12, 14 and 16. Fold portions 34 are substantially V-shaped and thus taper inwardly from the periphery 22, 24 or 26 to become more narrow at the end adjacent the center of the corresponding layer 12, 14 or 16. Fold portions 34 improve the fit of bra liner 10. They allow each layer 12, 14 and 16 to expand and contract as a mother's breasts change sizes during the nursing period.

The innermost wicking layer 12 is preferably composed of a thin cotton mesh or similar material which allows moisture leakage to be wicked through this layer 12 into the adjacent middle absorbing layer 14. A suitable wicking material is a thin hydrophobic material which is liquid permeable and thus allows fluid to wick through it to absorbing layer 14, while remaining dry and comfortable against the wearer's skin, similar in fashion to a stay-dry lining found in disposable diapers.

Figure 4:
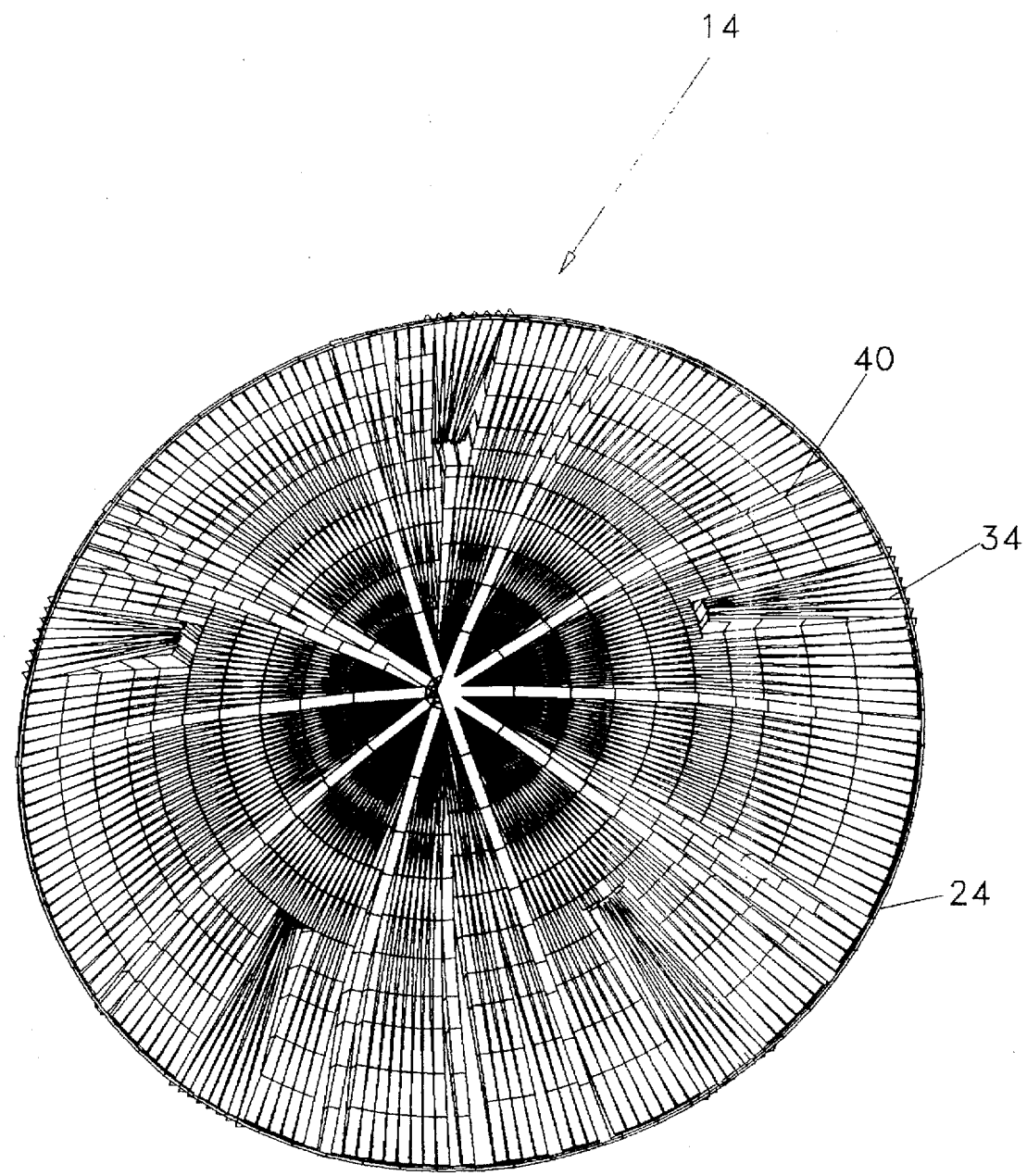
FIG. 4 is a top or front view of the middle absorbent layer of the bra liner of FIG. 1.

Absorbent middle layer 14, as seen in FIG. 4, is composed of a material similar to that found in disposable diapers and includes quilting 40 which creates small air pockets that allow air to pass through the liner 10 and keep the wearer's breasts dry. Such a material has an ultra high fluid absorbing composition, such as cellulose, thermoplastic copolymers, foam or similar materials that contain or is impregnated with a gelling agent, such as polyacrylate grafted starch, maleic anhydride-based copolymers, or similar materials, so as to absorb the most fluid with the least amount of expansion.

Figure 3:
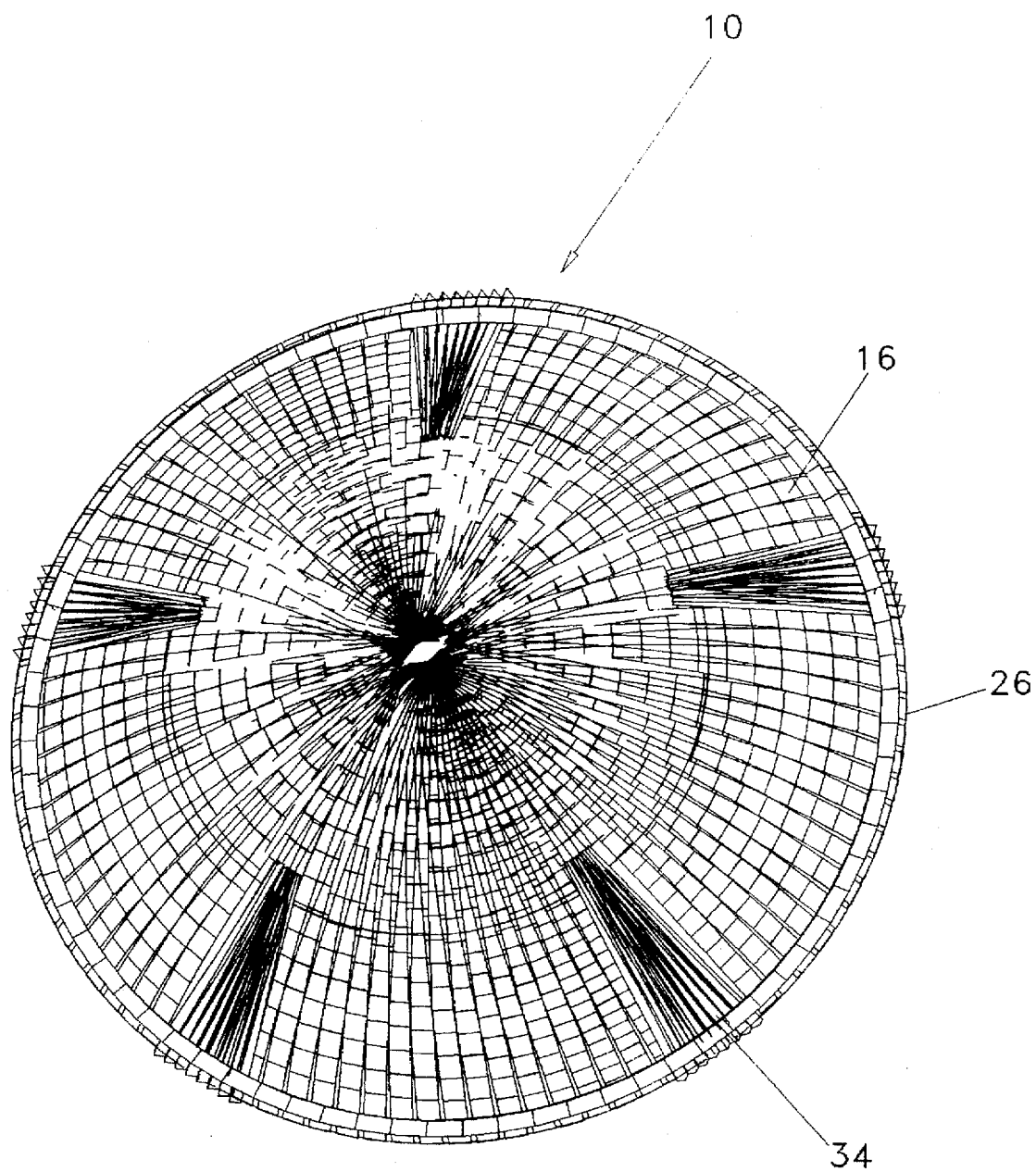
FIG. 3 is a top or front view of the bra liner of FIG. 1 showing the outer moisture resistant layer thereof.

Outer moisture resistant layer 16, as seen in FIG. 3, prevents leakage from liner 10 onto the wearer's clothes. Outer layer 16 is preferably composed of a light plastic or rubber latex or similar material that will expand or stretch if the wearer's breast expands when producing milk and will contract as the wearer's breast contracts during and after nursing. Also, the material does not rustle or crinkle when flexed or deformed.

Figure 5:
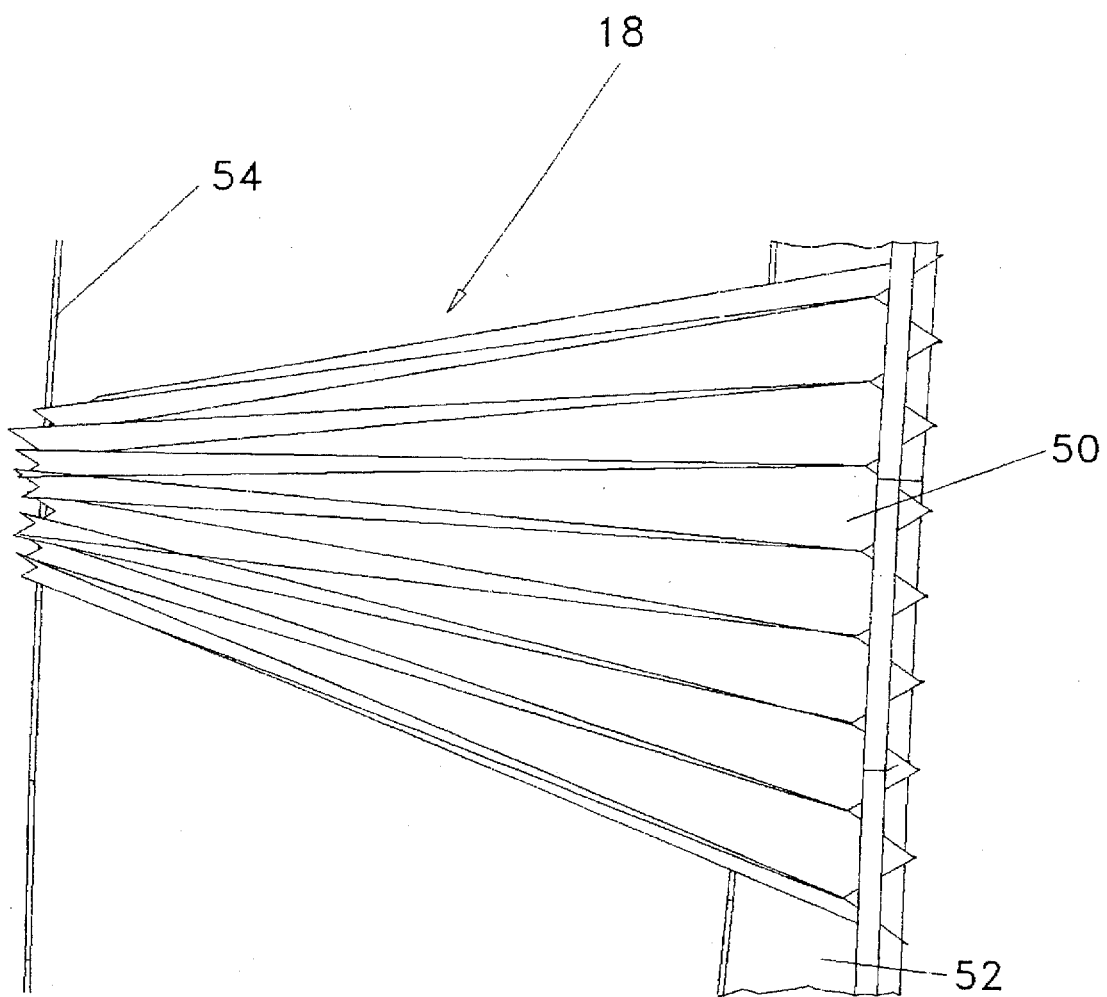
FIG. 5 is a fragmentary view of the structural member of the bra liner of FIG. 1 showing a portion of the elastic band and a V-shaped fold portion extending therefrom.

Structural member 18 includes another set of spaced apart V-shaped accordion fold portions 50 connected to an outer elastic band 52, as best seen in FIGS. 2 and 5. Elastic band 52 is circular and connected to the peripheries 22, 24 and 26 of layers 12, 14 and 16. Band 52 maintains the liner's shape and prevents it from shifting out of position when the bra is worn. Fold portions 50 are identical to fold portions 34 but extend inwardly from elastic band 52 and are connected at a free end by a second band 54. Fold portions 50 further help to maintain the shape of liner 10, prevent it from shifting out of position and make liner 10 size adjustable. Fold portions 50 are preferably formed from a material that increases ventilation in the liner 10.

A fastening member 60, such as a Velcro® patch or snaps can also be included on the outer surface of moisture resistant layer 16 (the surface adjacent the bra cup when in use) to allow liner 10 to be fastened and secured within the cup of a nursing bra.

It is to be understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. A bra cup liner comprising:
    an absorbent material layer shaped for placement in a bra cup presenting a periphery;
    a correspondingly shaped moisture resistant material layer presenting a periphery and being attached to said absorbent layer;
    a structural member attached to said peripheries of said layers for maintaining the shape of the liner, said structural member including a first band extending about said layers;
    a substantially V-shaped fold portion extending from said first band and tapering therefrom.

2. A bra cup liner as claimed in claim 1, further comprising:
    a correspondingly shaped wicking away layer attached to said absorbent layer for wicking moisture into said absorbent layer.

3. A bra cup liner as claimed in claim 1, wherein said band is elastic.

4. A bra cup liner as claimed in claim 1 wherein said structural member further comprises a second band spaced from said first band and extending about said layers, said fold portion extending between said first band and second band.

5. A bra cup liner as claimed in claim 4 further comprising a plurality of said V-shaped fold portions extending between said first and second bands, said fold portions spaced one from the other.

6. A bra cup liner comprising:
    an absorbent material layer shaped for placement in a bra cup presenting a periphery;
    a correspondingly shaped moisture resistant material layer presenting a periphery and being attached to said absorbent layer;
    a structural member presenting a periphery and being associated with said absorbent and moisture resistant layers for maintaining the shape of the liner;
    at least one of said material layers including at least one V-shaped material fold portion extending from said corresponding layer's periphery and tapering therefrom.

7. A bra cup liner as claimed in claim 6, wherein said structural member includes an elastic band.

8. A bra cup liner as claimed in claim 6 wherein said structural member comprises:
    a first elastic band attached about a periphery of at least one of said absorbent or moisture resistant material layers;
    a second elastic band spaced from said first elastic band and attached to at least one of said absorbent or moisture resistant material layers, said at least one V-shaped fold portion extending between said bands.

9. A bra cup liner as claimed in claim 8 further comprising a plurality of said V-shaped fold portions extending between said first and second bands, said fold portions spaced one from the other.

10. A bra cup liner, comprising:
    a plurality of cup-shaped coextensive material layers attached together with each said layer presenting a circular periphery, said layers comprising:
    a first material layer formed of wicking material for wicking away moisture into a second absorbent layer and a third moisture resistant layer attached to said absorbent layer; and
    structural means attached to said layers for maintaining the shape of said liner, said means including a band attached to said layers and a substantially V-shaped material fold portion tapering inwardly from said band.

11. A bra cup liner as claimed in claim 10, wherein at least one of said layers includes a V-shaped material fold portion formed therein which tapers inwardly from said periphery of said layer.

12. A bra cup liner as claimed in claim 11, wherein each said layer includes a plurality of said fold portions formed therein and said band has a plurality of said fold portions extending therefrom.

13. A bra cup liner as claimed in claim 10, wherein said band is elastic.

14. A bra cup liner, comprising:
    a plurality of cup-shaped coextensive layers attached together, with each said layer presenting a circular periphery, said layers comprising:

a first layer of said coextensive layers formed of wicking material for wicking away moisture into a second absorbent layer of said coextensive layers and a third moisture resistant layer of said coextensive layers being attached to said second absorbent layer;

at least one of said layers including a substantially V-shaped fold portion formed therein, said fold portion tapering inwardly from said corresponding periphery of said layer.

15. A bra cup liner as claimed in claim 14, wherein said first layer is proximal a wearer of the bra and said third layer is distal the wearer of the bra.

16. A bra cup liner as claimed in claim 14, wherein said second layer is intermediate said first and third layers.

17. A bra cup liner as claimed in claim 14 further comprising a structural member positioned intermediate a pair of adjacent layers of said coextensive layers for maintaining the shape of the liner.

18. A bra cup liner as claimed in claim 17 wherein said structural member comprises:

an elastic band attached to said periphery of said adjacent layers;

a plurality of substantially V-shaped material fold portions extending from said band.

* * * * *